(12) United States Patent
Rogers

(10) Patent No.: US 11,786,141 B2
(45) Date of Patent: Oct. 17, 2023

(54) SYSTEM, METHOD, AND APPARATUS FOR DETECTING TUBE MISPLACEMENT IN A PATIENT'S AIRWAY

(71) Applicant: Avent, Inc., Alpharetta, GA (US)

(72) Inventor: Daniel J. Rogers, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 481 days.

(21) Appl. No.: 16/291,124

(22) Filed: Mar. 4, 2019

(65) Prior Publication Data

US 2020/0282165 A1 Sep. 10, 2020

(51) Int. Cl.
*A61B 5/06* (2006.01)
*A61M 16/04* (2006.01)
(Continued)

(52) U.S. Cl.
CPC ............. *A61B 5/064* (2013.01); *A61B 1/00* (2013.01); *A61B 1/06* (2013.01); *A61B 1/07* (2013.01); *A61B 5/0084* (2013.01); *A61B 5/061* (2013.01); *A61M 16/0051* (2013.01); *A61M 16/0411* (2014.02); *A61M 16/0463* (2013.01);
(Continued)

(58) Field of Classification Search
CPC .......... A61M 16/0463; A61M 16/0411; A61M 16/0477; A61M 16/0051; A61M 16/0486; A61J 15/0084; A61J 15/0003; A61J 15/0388; A61J 15/003; A61B 5/0059; A61B 5/064
See application file for complete search history.

(56) References Cited

U.S. PATENT DOCUMENTS 4,836,214 A 6/1989 Sramek
4,921,481 A 5/1990 Danis et al.
(Continued)

FOREIGN PATENT DOCUMENTS

CN 102755184 B * 5/2014
CN 204798472 U * 11/2015
(Continued)

OTHER PUBLICATIONS

Anonymous, "Multiple lumen extruded shafts for endoscope devices and methods of making the same", IP.com No. IPCOM000225849D, IP.com Electronic Publication Date: Mar. 8, 2013 (Year: 2013).*
(Continued)

*Primary Examiner* — Douglas Kay
(74) *Attorney, Agent, or Firm* — Dority & Manning, P.A.

(57) ABSTRACT

Enteral tubes, tube tip detection systems, and methods for detecting tube misplacement are provided. For example, a tube tip detection system comprises an enteral tube having a tip and a first light disposed at the tip that is illuminated as the enteral tube is inserted into a patient to indicate to a user of the system whether the tip is misplaced in the patient's airway. Similarly, enteral tubes are provided that comprise a tip, a length, and a light that is continuously illuminated as the enteral tube is inserted into a patient. Methods for detecting a tube misplacement in a patient's airway include embedding a light into an enteral tube, inserting the enteral tube into the patient through the patient's nose or mouth, and monitoring a location of the light as the enteral tube is inserted into the patient to determine if the tube is traveling into the patient's airway.

15 Claims, 8 Drawing Sheets

(51) Int. Cl.
*A61M 16/00* (2006.01)
*A61B 1/07* (2006.01)
*H05B 45/48* (2020.01)
*A61N 5/06* (2006.01)
*A61B 5/00* (2006.01)
*A61B 1/00* (2006.01)
*A61B 1/06* (2006.01)
*A61J 15/00* (2006.01)

(52) U.S. Cl.
CPC .......... *A61M 16/0477* (2014.02); *A61N 5/06* (2013.01); *H05B 45/48* (2020.01); *A61J 15/0003* (2013.01); *A61J 15/0084* (2015.05); *A61M 16/0486* (2014.02); *A61M 16/0488* (2013.01); *A61M 2016/003* (2013.01)

(56) References Cited

U.S. PATENT DOCUMENTS

| | | | | |
|---|---|---|---|---|
| 5,662,712 | A * | 9/1997 | Pathak | B29C 70/74 606/195 |
| 6,334,064 | B1 | 12/2001 | Fiddian-Green | |
| 6,357,447 | B1 | 3/2002 | Swanson et al. | |
| 6,929,600 | B2 * | 8/2005 | Hill | A61B 1/00052 600/120 |
| 7,757,695 | B2 * | 7/2010 | Wilson | A61M 25/01 128/899 |
| 7,818,155 | B2 | 10/2010 | Stuebe et al. | |
| 7,992,573 | B2 * | 8/2011 | Wilson | A61B 5/06 128/899 |
| 8,147,486 | B2 | 4/2012 | Honour et al. | |
| 8,613,702 | B2 | 12/2013 | Feer et al. | |
| 8,986,230 | B2 | 3/2015 | Nishtala | |
| 9,179,971 | B2 | 11/2015 | Kirschenman | |
| 9,226,878 | B2 | 1/2016 | Elia et al. | |
| 9,295,395 | B2 | 3/2016 | Elia et al. | |
| 9,532,739 | B2 | 1/2017 | Bennett-Guerrero | |
| 9,610,227 | B2 | 4/2017 | Elia | |
| 9,642,779 | B2 | 5/2017 | Elia et al. | |
| 9,713,579 | B2 | 7/2017 | Elia et al. | |
| 10,500,011 | B2 * | 12/2019 | Tan | A61B 90/30 |
| 2003/0078476 | A1 * | 4/2003 | Hill | A61B 1/00052 600/160 |
| 2006/0036164 | A1 * | 2/2006 | Wilson | A61B 5/06 600/424 |
| 2006/0241395 | A1 | 10/2006 | Kruger et al. | |
| 2007/0118014 | A1 * | 5/2007 | Fuerst | A61B 1/00167 600/138 |
| 2008/0027408 | A1 * | 1/2008 | Wilson | A61B 5/0059 604/500 |
| 2008/0097179 | A1 | 4/2008 | Russo | |
| 2008/0167607 | A1 | 7/2008 | Pfeiffer et al. | |
| 2008/0249467 | A1 | 10/2008 | Burnett et al. | |
| 2010/0179417 | A1 * | 7/2010 | Russo | A61M 39/08 600/424 |
| 2011/0270080 | A1 | 11/2011 | Crane | |
| 2012/0016256 | A1 | 1/2012 | Mabary et al. | |
| 2012/0277619 | A1 | 11/2012 | Starkebaum et al. | |
| 2013/0225946 | A1 | 8/2013 | Feer et al. | |
| 2015/0190649 | A1 * | 7/2015 | Gelfand | A61N 5/0624 385/100 |
| 2015/0328031 | A1 * | 11/2015 | Rokde | A61M 25/007 600/104 |
| 2016/0015544 | A1 * | 1/2016 | Holsten | A61F 5/0089 600/37 |
| 2016/0113843 | A1 | 4/2016 | Elia et al. | |
| 2016/0129223 | A1 | 5/2016 | Kirschenman | |
| 2016/0331298 | A1 | 11/2016 | Burnett et al. | |
| 2017/0071502 | A1 | 3/2017 | Bennett-Guerrero | |
| 2017/0202750 | A1 | 7/2017 | Elia | |
| 2018/0064611 | A1 * | 3/2018 | Kirn | A61B 1/0684 |
| 2018/0078195 | A1 | 3/2018 | Sutaria et al. | |
| 2018/0161249 | A1 | 6/2018 | Elia et al. | |
| 2018/0289536 | A1 | 10/2018 | Burnett | |

FOREIGN PATENT DOCUMENTS

CN 111819861 A * 10/2020 .......... H04R 1/1016
WO WO 92/17150 10/1992

OTHER PUBLICATIONS

W. J. Cassarly, "Light Pipe Design", Illumination Engineering: Design with Nonimaging Optics, First Edition. R. John Koshel. © 2013 the Institute of Electrical and Electronics Engineers. Published 2013 by John Wiley & Sons, Inc. (Year: 2013).*

International Search Report and Written Opinion for PCT/US2020/018630, dated May 28, 2020, 14 pages.

* cited by examiner

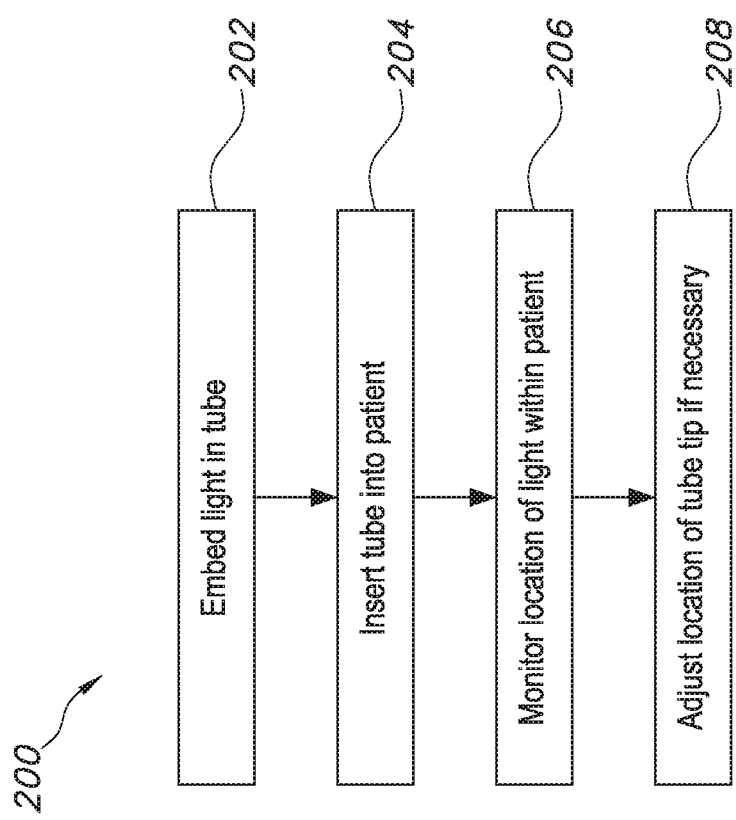

SYSTEM, METHOD, AND APPARATUS FOR DETECTING TUBE MISPLACEMENT IN A PATIENT'S AIRWAY

FIELD

The present subject matter relates generally to a system, method, and apparatus for administering fluids to body cavities and, more particularly, to such systems, methods, and apparatus utilizing light to detect whether a tube is incorrectly inserted into a patient's airway.

BACKGROUND

Physicians and other health care providers frequently use catheters, which include tubes inserted into the human body, to treat patients. A nasogastric (NG) tube is one type of tube that is placed in the gastrointestinal tract for patients experiencing a variety of ailments. NG tubes are placed through the nasal cavity and are intended to traverse through the esophagus down into the stomach and into the small bowel, if desired. As the tube travels through the oropharynx and hypopharynx, the anatomy splits into the trachea and the esophagus. Tubes commonly are misplaced into the trachea, which can result in pneumonia, pneumothoraces, or even death. As such, there is a critical need for a way to determine when the tube has taken the path of the trachea as opposed to the desired path of the esophagus.

In some cases, health care providers use X-ray machines to gather information about the location of the catheters within the body. There are several disadvantages in using X-ray machines. For instance, X-rays from these machines are a known carcinogen, if received in sufficient doses. Also, X-ray machines are relatively large and heavy, consume a relatively large amount of energy, and may expose the patient to a relatively high degree of radiation. Moreover, these machines are typically not readily accessible for use because, due to their size, they are usually installed in a special X-ray room. This room can be relatively far away from the patient's room. Therefore, health care providers may find it inconvenient to use these machines for their catheter procedures. Further, it can be inconvenient to transport these machines to a patient's home for home care catheter procedures. As such, X-ray confirmation of the tube tip position may be performed only when the position is uncertain, and the enteral tube position more commonly is checked by assessing the pH of tube aspirate. However, it can be difficult to determine a practical pH cutoff level for reliable confirmation of NG tube placement, particularly for pediatric patients.

In other cases, electromagnetism is used to monitor the location or position of the enteral tube tip. For example, an electromagnetic stylet inserted into the patient's body with the enteral tube may provide real-time location information on the tube tip placement within a patient's anatomy. A receiver unit outside the body detects an electromagnetic field transmitted by the stylet and provides on-screen visualization and, thereby, immediate feedback on tube placement. Nevertheless, due to, e.g., variation in placement of the receiver unit and user misinterpretations of the feedback from the electromagnetic stylet, a health care provider can fail to recognize a misplacement of the enteral tube tip within the patient's airway.

Thus, recognition of the airway when placing an enteral tube is an important way to prevent harm to a patient, and the art is continuously seeking new and improved systems, apparatus, and methods for determining a location of a tip of a catheter, such as an NG tube, being inserted into a patient. For instance, an improved enteral tube, such as an NG tube, incorporating means for detecting a tip of the enteral tube to determine whether the enteral tube is being improperly inserted in a patient's airway would be useful. More particularly, illuminating the tip of an enteral tube, such as an NG tube, such that the location of the tip can be determined from outside the patient's body would be desirable. Moreover, methods for detecting a tube misplacement in a patient's airway utilizing an illuminated tube tip would be advantageous.

SUMMARY

Objects and advantages of the invention will be set forth in part in the following description, or may be obvious from the description, or may be learned through practice of the invention.

In one aspect, the present subject matter is directed to a tube tip detection system that comprises an enteral tube having a tip and a first light disposed at the tip. The first light is illuminated as the enteral tube is inserted into a patient to indicate to a user of the tube tip detection system whether the tip is misplaced in the patient's airway. It should also be understood that the tube tip detection system may further include any of the additional features as described herein.

In another aspect, the present disclosure is directed to an enteral tube that comprises a tip, a length, and a light. The light is continuously illuminated as the enteral tube is inserted into a patient. It should also be appreciated that the enteral tube may further include any of the additional features as described herein.

In yet another aspect, the present disclosure is directed to a method for detecting a tube misplacement in a patient's airway. The method comprises embedding a light into an enteral tube, inserting the enteral tube into the patient through the patient's nose or mouth, and monitoring a location of the light as the enteral tube is inserted into the patient to determine if the enteral tube is traveling into the patient's airway. It should also be understood that the method may further include any of the additional features as described herein.

These and other features, aspects and advantages of the present subject matter will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIG. 8 provides a flow diagram illustrating a method for detecting a tube misplacement in a patient's airway.

DETAILED DESCRIPTION

Figure 1:
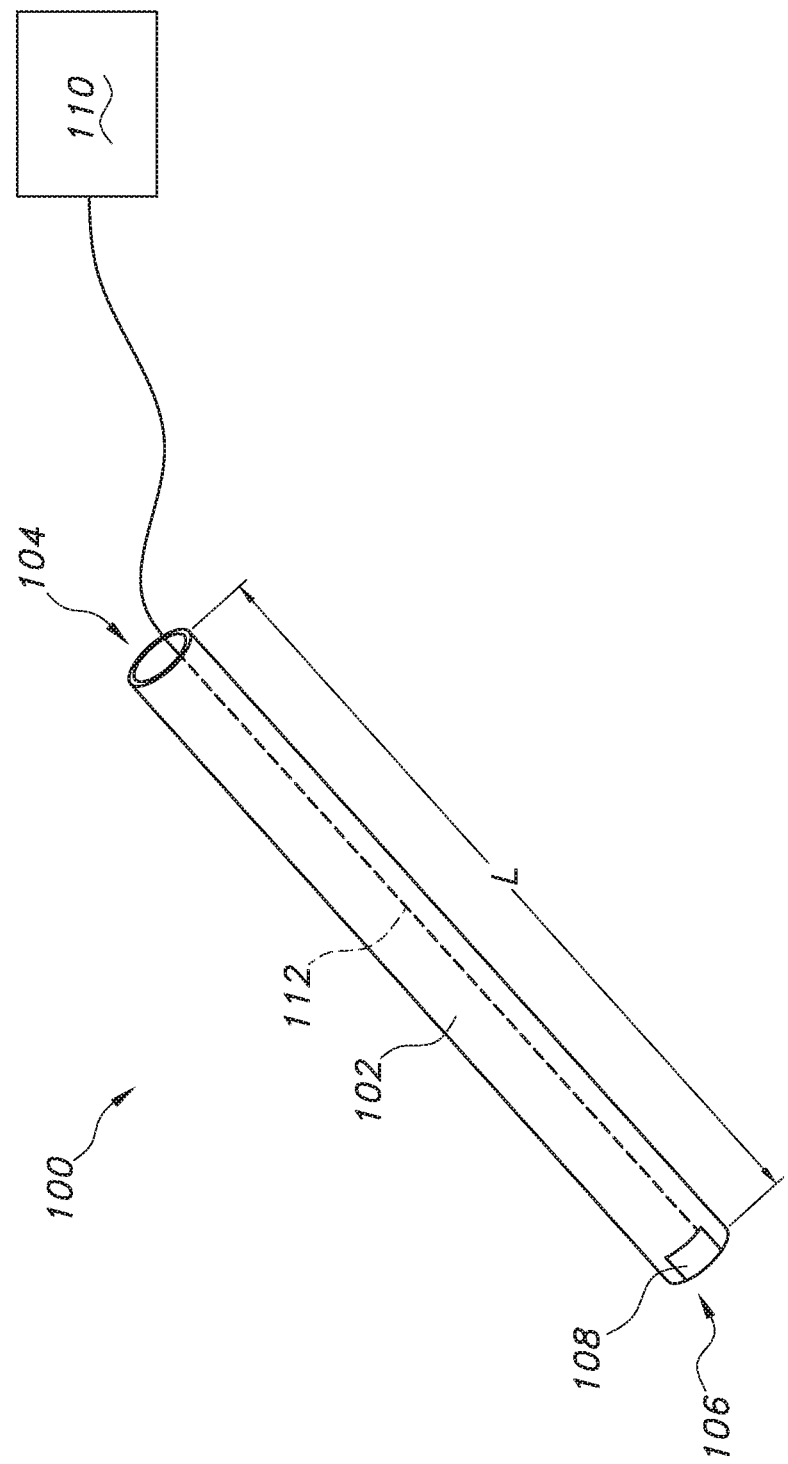
FIG. 1 provides a schematic view of a tube tip detection system having an enteral tube, a light source embedded in the enteral tube, and a wire or cable extending from the light source to a power source, according to an exemplary embodiment of the present subject matter.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Generally, the present subject matter provides catheters for intubating patients having one or more light sources thereon to determine, using the location and/or intensity of light from the light source(s) that is transmitted through the patients' tissues, anatomy, etc. and appears on the patients' skin, whether the catheter is being inserted into the patient's airway. Certain catheters are inserted into through the patient's nose or mouth and extend into the patient's gastrointestinal tract and, thus, also may be referred to as enteral catheters or enteral tubes. More particularly, enteral tubes inserted through the patient's nose are called nasogastric (NG) tubes, which typically are feeding tubes. The feeding tube tip, through which a fluid flows into the patient, is disposed in the stomach or intestines, and a feeding source delivers liquid nutrient, liquid medicine, or a combination of the two to the patient. Because erroneous placement of the tube tip may injure or harm the patient, particularly if the tube is misplaced into the patient's airway, it is important to place the tip of the tube at the proper location within the patient's body. Thus, the present subject matter provides enteral tubes having one or more light sources, which are continuously illuminated as the enteral tube is inserted into a patient such that light from the light source(s) appears on the patient's skin. By monitoring the location and/or intensity of the light on the patient's skin, a user (such as a health care provider) can determine whether the enteral tube is being misplaced into the patient's airway, where the light will deviate in position and be brighter (have a higher or greater intensity) compared to the location and intensity in the correct placement area, the patient's esophagus and gastrointestinal tract. Further, the present subject matter provides systems and methods for detecting a tube misplacement in a patient's airway.

Figure 2:
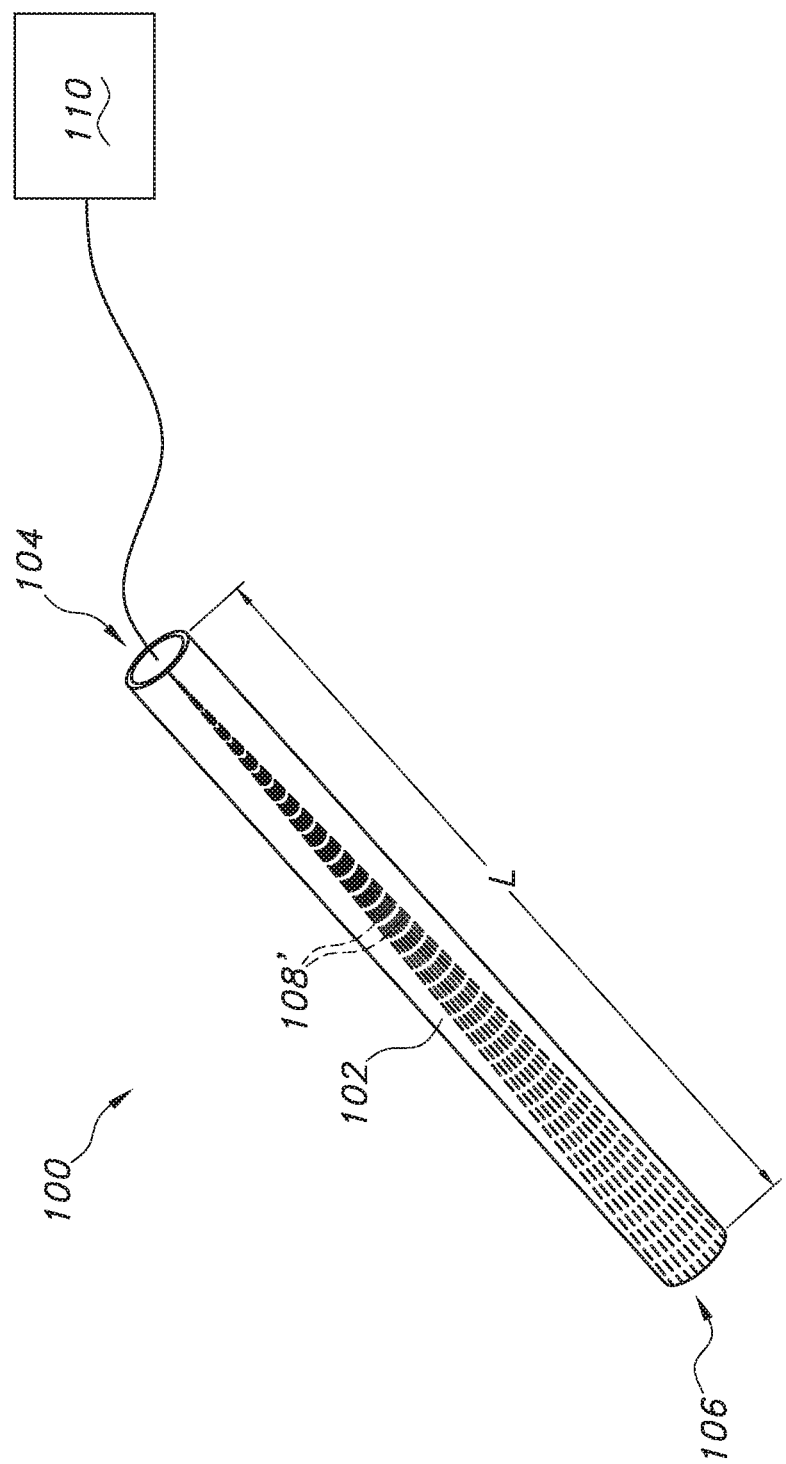
FIG. 2 provides a schematic view of a tube tip detection system having an enteral tube, a plurality of optical fibers embedded in the enteral tube, and a light source in operative communication with the plurality of optical fibers, according to an exemplary embodiment of the present subject matter.

Referring now to the drawings, FIGS. 1 and 2 each illustrate an exemplary embodiment of a tube tip detection system 100 having an enteral tube 102 that includes a proximal end or head 104 and a distal end or tip 106. The enteral tube 102 has a length L between the proximal end 104 and the tip 106. Further, the enteral tube 102 should have an appropriate diameter and be sufficiently flexible for insertion through, e.g., a patient's nose or mouth and into the patient's gastrointestinal tract. For instance, the enteral tube 102 should have a size within a range of five to seven French (5 Fr to 7 Fr) for pediatric patients and within a range of eight to twelve French (8 Fr to 12 Fr) for adult patients.

In exemplary embodiments the enteral tube 102 is a nasogastric (NG) tube, which, through a process called nasogastric intubation, is inserted through a patient's nose into the patient's stomach. In other exemplary embodiments, the enteral tube 102 is an orogastric (OG) tube inserted during orogastric intubation through the patient's mouth into the stomach. Alternatively, the tube tip 106 may extend into the patient's intestines rather than the stomach. Whether the tip 106 is disposed in the stomach or intestines may depend on, e.g., the specific needs of the patient. For typical nasogastric intubations or orogastric intubations, the tube tip 106 should be in a sub-diaphragmatic position in the stomach, e.g., at least ten (10) centimeters (cm) beyond the gastro-esophageal junction (GOJ), also known as the oesophagogastric junction, which is the part of the gastrointestinal tract where the esophagus and stomach are joined.

As discussed herein, misplacement of the tip 106 in the patient's airway, e.g., the bronchi or the lungs, rather than in the patient's gastrointestinal tract is a complication of nasogastric or orogastric intubation. To avoid such misplacement, the present subject matter provides enteral tubes 102 with lights or lighting components to detect whether the tube tip 106 is being misplaced in the patient's airway. In the exemplary embodiment depicted in FIG. 1, a first light 108 is disposed at the tip 106, and a power source 110 is operatively connected to the first light 108 to power or energize the first light 108. For instance, a means for conducting power to the first light 108, such as a cable, cord, or wire 112, is embedded within the enteral tube 102 and extends along the tube's length from the first light 108 to, e.g., the proximal end 104 of the tube 102, where the wire 112 exits the tube 102 and connects to the power source 110. In exemplary embodiments, the first light 108 comprises a light emitting diode (LED) or group of LEDs, which can be fabricated in small sizes, such as in micrometer (μm) to millimeter (mm) sizes, and then embedded in enteral tubes 102.

In other exemplary embodiments, such as the embodiment shown in FIG. 2, the first light 108 comprises a plurality of optical fibers 108'; that is, the first light 108 is a fiber optic light. In such embodiments, the tube tip detection system 100 comprises a light source 110, which transfers light to the optical fibers 108' and thereby light or illuminate the first light 108. More particularly, fiber optic lighting typically uses one or more optical fibers, such as optical fibers 108', as a light guide or light pipe that transmits light from a source through the fiber to a remote location, e.g., the tip 106 of the enteral tube 102. The light may be emitted from the ends of the optical fibers 108' to create a small spotlight effect (also called "end glow") or emitted from the outside of the optical fibers 108' along their length (also called "side glow"). Alternatively or additionally, a diffuser may be disposed in the enteral tube 102 to disperse the light from the optical fibers 108' radially about the tube 102 and thereby orient the light toward the surface of the patient's skin. Thus, to form the first light 108 at the tip 106 of the enteral tube 102, the light may be emitted from the ends of the optical fibers 108' or from the sides of the optical fibers 108' only at or near the tip 106, i.e., no side glow pasta certain distance from the tube tip 106. The optical fibers 108' consist of a core that transmits the light and an optical cladding that traps the light in the core of the fiber. Typically, optical fibers have large cores with thin claddings to maximize coupling of the light from the illuminator into the fiber. The core is the component that transmits the light, and the cladding is tightly fitted around the core and has a low refractive index such that light beams that graze the cladding at shallow angles reflect back into the core. In addition, most optical fibers have a third layer forming a protective jacket, which is black, clear, or translucent white. A black, non-transparent protective jacket is used, e.g., with end-emitting optical fibers 108', and a clear or translucent white protective jacket is used, e.g., with side-emitting optical fibers 108'.

As the enteral tube 102 is inserted into a patient, e.g., through the patient's nose or mouth, the first light 108 is illuminated, e.g., power is supplied from the power source 110 to the first light 108 or light is supplied from the light source 110 to the first light 108, such that light shines or radiates from the first light 108 at the tip 106 of the enteral tube 102. Light from the first light 108 shines through the patient's tissues, etc. to indicate the location of the tube tip 106 to a user of the tube tip detection system 100 such that the user can determine whether the tip 106 is misplaced in a patient's airway or is properly placed in the patient's esophagus or gastrointestinal tract. The user may be a health care provider, such as a physician, clinician, nurse, etc.

Thus, the present subject matter utilizes light transmission through the patient's skin to give the placing health care provider (i.e., the user of the system 100) an indication of where the enteral tube 102 is inside of the patient's body. As light from the first light 108 travels through the patient's body, anatomical structures absorb and reflect the light, resulting in a glow that shows up on the surface of the patient's skin. More particularly, the glow through the patient's skin is tinted red due to, e.g., capillaries and other blood-carrying tissues the light passes through as it travels from the first light 108 through the patient's skin. It will be appreciated that the present subject matter may be particularly suitable for use in pediatric patients, whose tissues and other anatomical structures are thinner than those of adult patients, which allows the light to transmit more easily through such structures. However, the present subject matter also can be adapted for use in adult patients, as well as non-human patients, e.g., in a veterinary practice.

The light source, i.e., the first light 108 in the embodiments of FIGS. 1 and 2, can be a constant indicator of the location of the tip 106 of the enteral tube 102. That is, the first light 108 can be continuously illuminated from the time the tip 106 is inserted into the patient's body until the tip 106 is located in a proper final position in the patient's body, e.g., in the patient's stomach or small intestine. Accordingly, the first light 108 on the end of the enteral tube 102 can be active throughout the entire placement of the tube 102, creating a glowing "ball" or spot of red-tinted light on the surface of the patient's skin, and thereby be used to determine the location of the tube tip 106.

Figure 3:
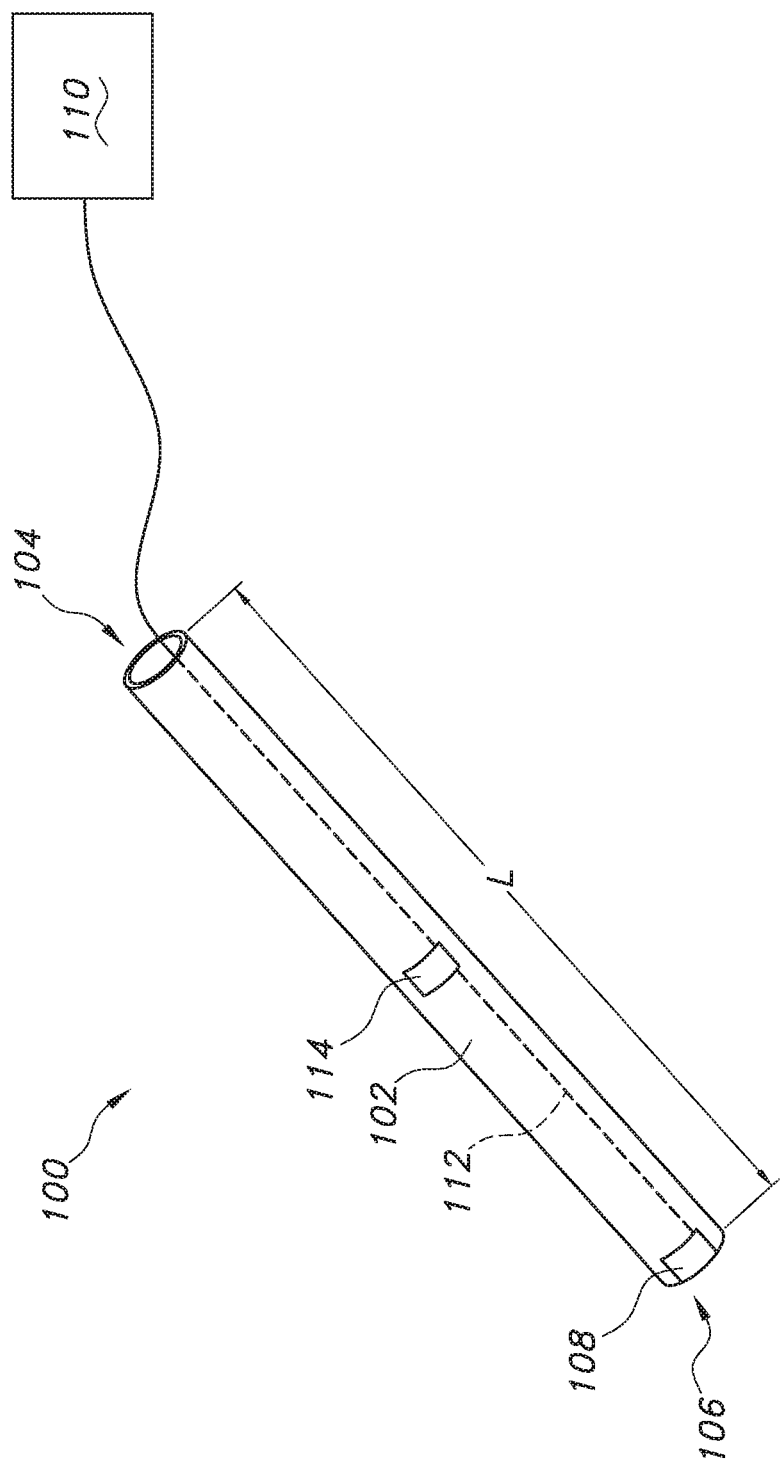
FIG. 3 provides a schematic view of a tube tip detection system having an enteral tube, a first light embedded in the enteral tube, and a second light embedded in the enteral tube, according to an exemplary embodiment of the present subject matter.
Figure 4:
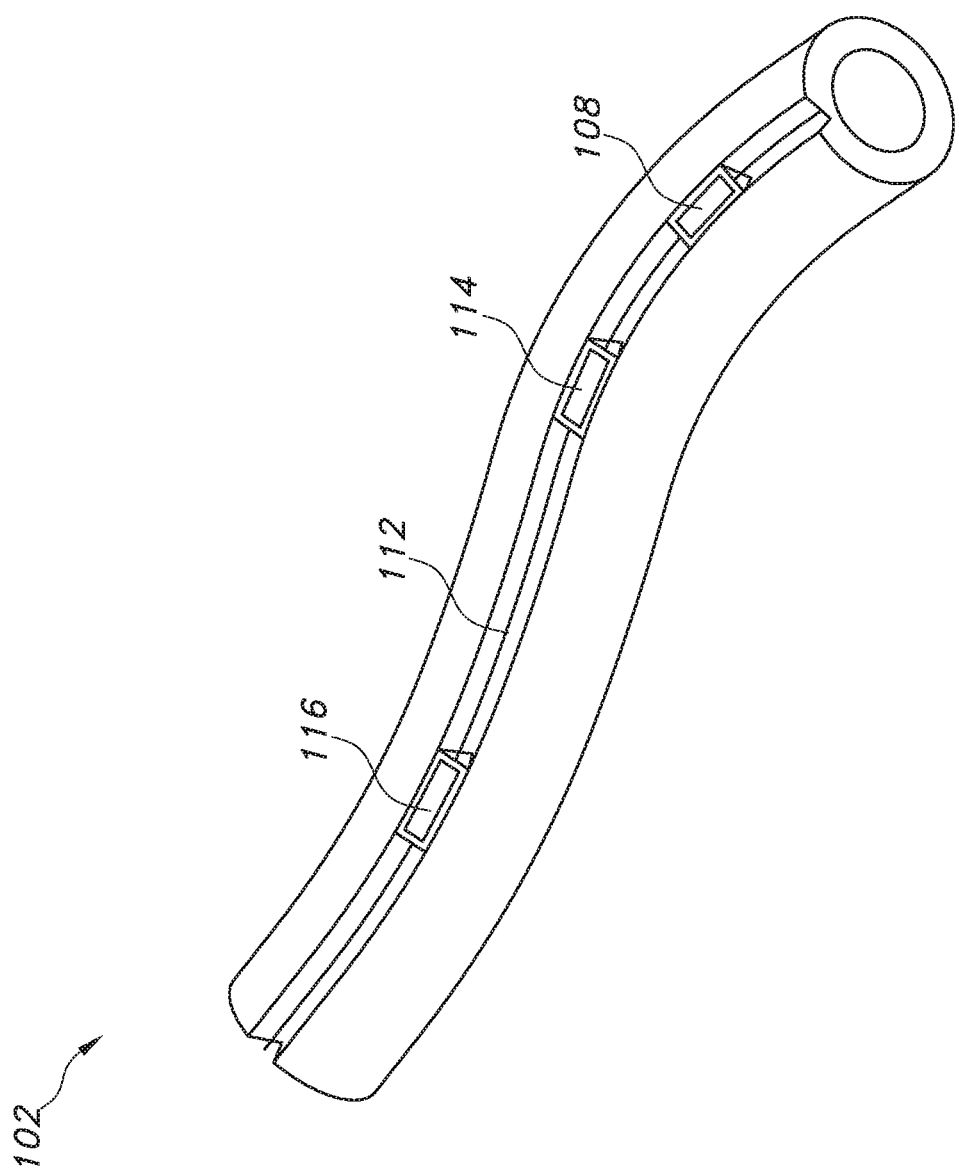
FIG. 4 provides a side perspective view of a portion of an enteral tube having a plurality of lights or lighting components disposed in a channel formed in a wall of the enteral tube.

FIGS. 3 and 4 illustrate other exemplary embodiments of the tube tip detection system 100. As shown, in some embodiments, the enteral tube 102 includes a plurality of light sources that are spaced apart from one another along the length L of the enteral tube 102. That is, light transmission through the patient's skin can be accomplished via a single, a series, or a group of light sources disposed on the enteral tube 102. As described above, each light or lighting component of the plurality of lights or lighting components may be an LED light, an optical fiber lighting component, or other suitable light source. Where a plurality of lights or lighting components are disposed in the enteral tube 102 along its length L, each light or lighting component may be the same type or of the same construction, but in other embodiments, different types of lights or lighting components may be used at different locations along the tube length L, e.g., a system 100 comprising two lights need not comprise two LED lights or two of another type of light source. Further, each light source may be configured and operated as described above with respect to the first light 108. For instance, each light source may be continuously illuminated as the enteral tube 102 is inserted into the patient such that, e.g., the location of the tube 102 within the patient may be continuously monitored.

The embodiment illustrated in FIG. 3 comprises the first light 108 disposed at the tube tip 106 and a second light 114 disposed along the length L at a position spaced apart from the tip 106. For example, the second light 114 may be disposed at a midpoint of the tube length L, i.e., halfway between the proximal end 104 and the tip 106. In other embodiments, such as depicted in FIG. 4, a third light or lighting component 116 also is disposed along the tube length L at a position spaced apart from the tip 106. In yet other embodiments, additional lights or lighting components also may be embedded in the enteral tube 102.

As shown in FIG. 4, to embed the lights 108, 114, and/or 116 in the enteral tube 102, in some embodiments a channel 118 is defined in the tube 102 during fabrication. Then, the first light 108, the second light 114, and/or the third light 116 are disposed within the channel 118. Next, a filler material may be disposed within the channel 118 around the first, second, and/or third lights 108, 114, 116 such that the light(s) 108, 114, 116 are embedded within the enteral tube 102. Such means for embedding the light(s) 108, 114, 116 in the enteral tube 102 may be best suited for embodiments in which the light(s) 108, 114, 116 are LED lights or the like. However, optical fibers 108' also may be disposed in the channel 118 to embed fiber optic lighting component(s) 108, 114, 116 in the enteral tube 102. The lights 108, 114, 116 may be embedded within the tube 102 in other ways as well.

Where the tube tip detection system 100 comprises more than one light or lighting component embedded in the enteral tube 102, each light of the plurality of lights embedded in the enteral tube 102 may be equally or unequally spaced apart from one another. For example, in some embodiments, like the exemplary embodiment of FIG. 4, the first light 108, the second light 114, and the third light 116 are unequally spaced apart from one another. That is, the distance, or portion of the tube length L, between the first and second lights 108, 114 is different from the distance between the second and third lights 114, 116. In other embodiments, the first light 108, the second light 114, and the third light 116 are equidistant from one another, i.e., the distance between the first and second lights 108, 114 is the same as the distance between the second and third lights 114, 116. Also as illustrated in FIG. 4, in some embodiments the first light 108 may not be disposed at the tip 106 of the enteral tube 102 but may be disposed along the tube length L such that the first light 108 is spaced apart from the tip 106. In such embodiments, no light may be disposed at the tip 106; that is, in some embodiments of the tube tip detection system 100, one or more lights are disposed on the tube 102 at a distance from the tube tip 106, with no light disposed precisely at the tip 106. Thus, a variety of placements or positions for the one or more lights may be used in various embodiments of the tube tip detection system 100.

Because the enteral tube 102 has a known length L, the position or location of the light glowing on the surface of the patient's skin relative to the patient's anatomy determines if the tube 102 has deviated to the patient's airway. Stated differently, the amount or length of the enteral tube 102 that has been inserted into the patient together with the location of the light from light(s) 108, 114, 116 transmitted through the patient's tissues conveys to a user of the tube tip detection system 100 whether the tube tip 106 is near the patient's airway and is possibly entering the patient's airway rather than continuing down a pathway 120 toward the patient's stomach or intestines, the intended destination of the tube tip 106. For example, it is known that bifurcation of the pathway 120 into the esophagus E and the trachea T occurs at a certain distance from the entrance to the nostril N in a patient P, with the certain distance varying between pediatric and adult patients. Knowing this distance for a given patient, as well as the length L of the enteral tube 102, the user can determine how much (or what length) of the tube 102 has been inserted into the patient and, thus, know whether the tube tip 106 is at or near the point where the trachea T branches off from the pathway 120, from which the tube 102 could be misplaced into the patient's airway.

Figure 5:
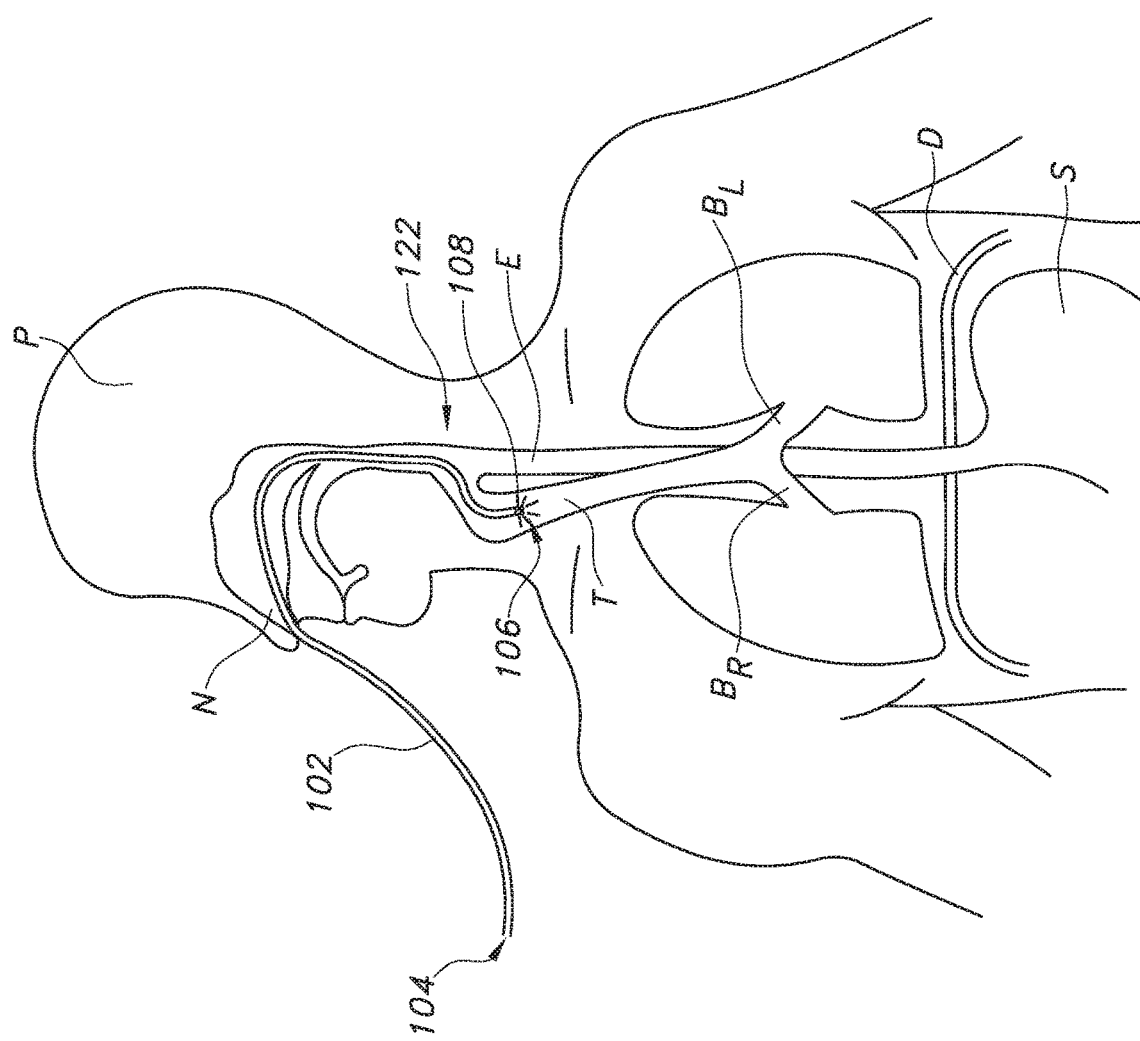
FIG. 5 provides a schematic view of a patient and an enteral tube of the present subject matter inserted through the patient's nostril and extending into the patient's trachea.
Figure 6:
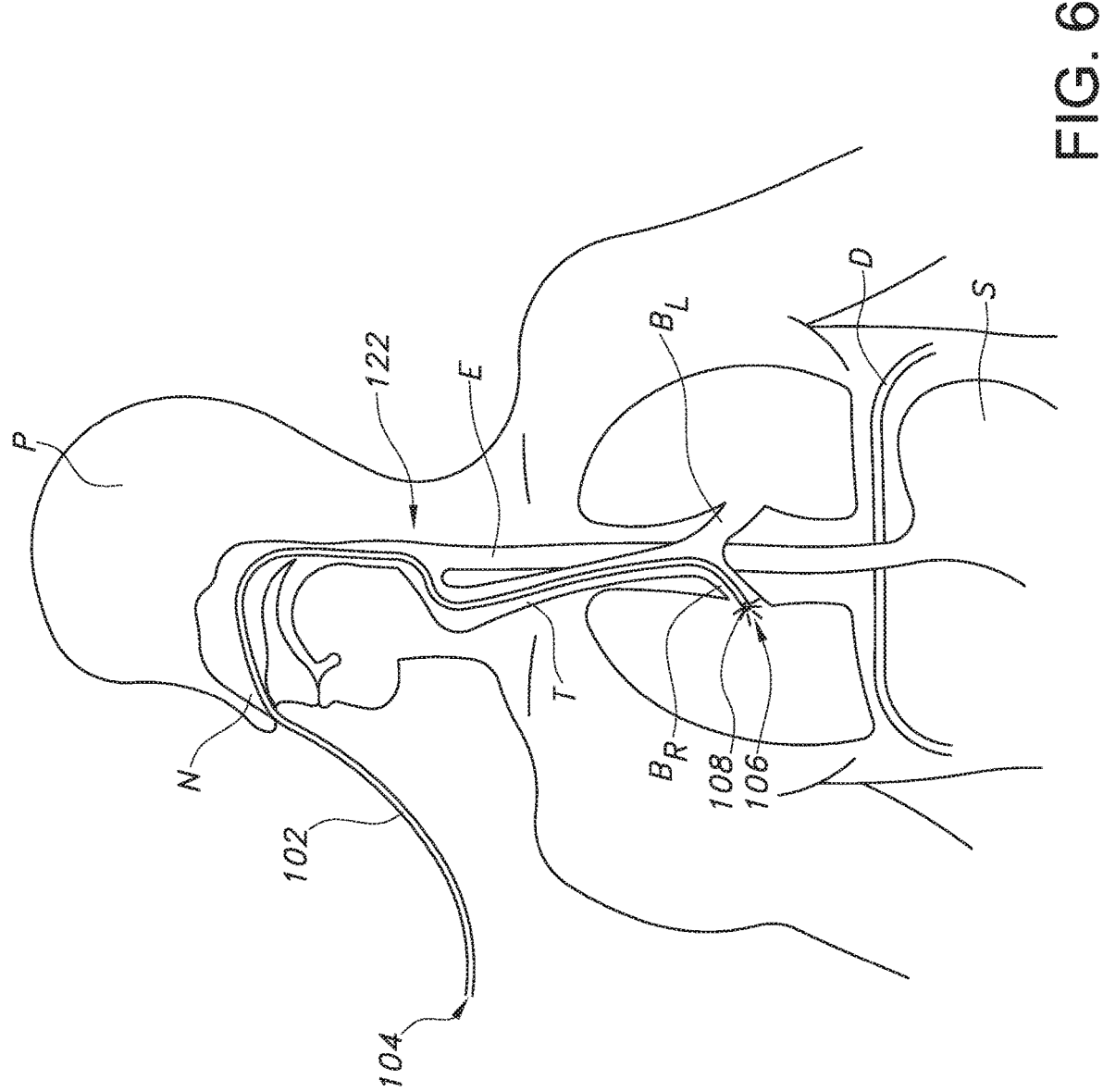
FIG. 6 provides the schematic view of the patient of FIG. 5, with the enteral tube misplaced within the patient's right brochi.
Figure 7:
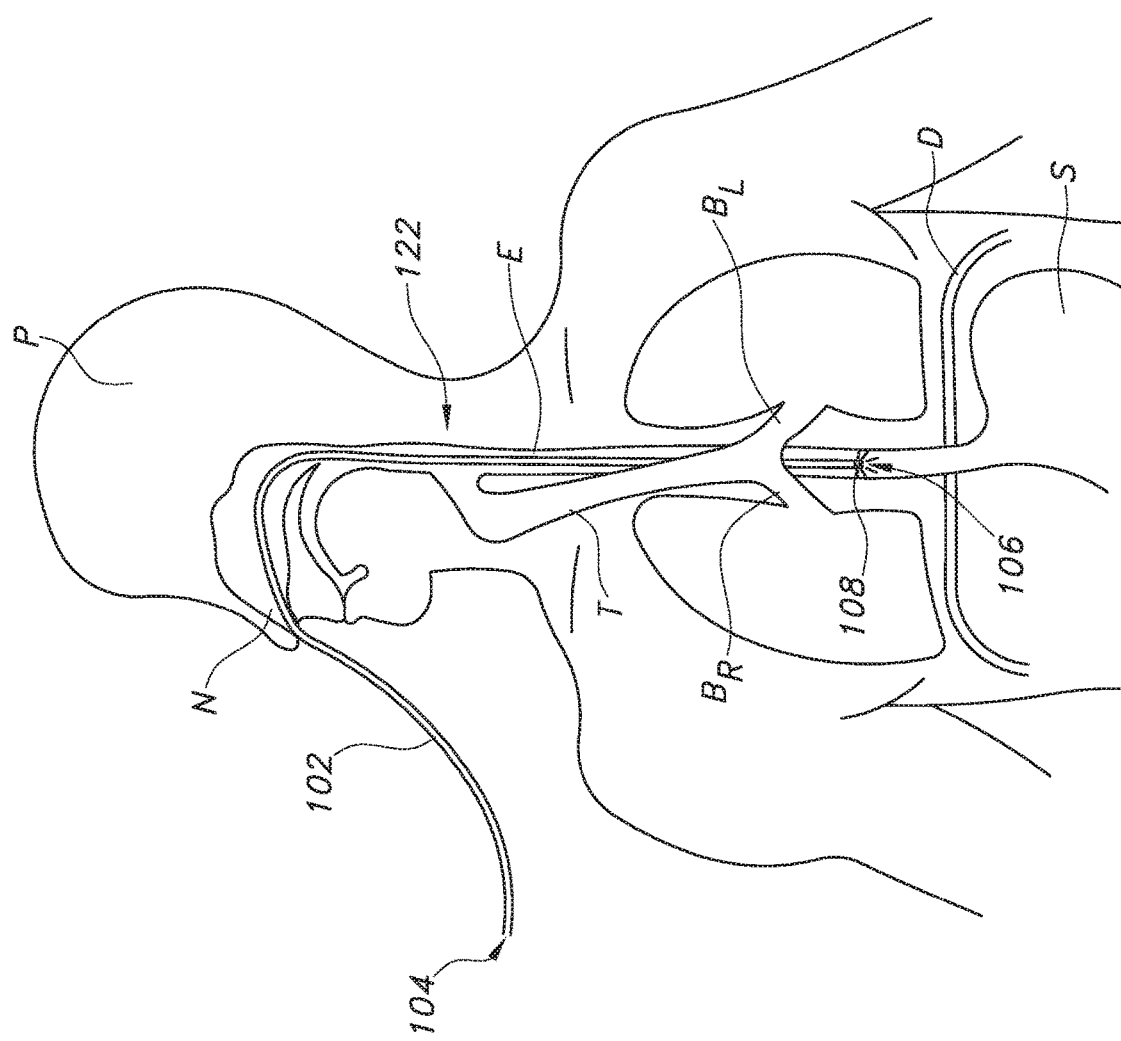
FIG. 7 provides the schematic view of the patient of FIG. 5, with the enteral tube correctly placed in the patient's esophagus and traveling toward the patient's stomach.

As an example, referring to FIG. 5, bifurcation typically occurs around 18-20 cm in adults; the area where bifurcation occurs may be referred to as a bifurcation zone 122. Further, the esophagus E is generally oriented in a vertical fashion and deviates into the stomach S past the diaphragm D, which is located at the xiphoid process. Thus, for nasogastric intubation of an adult patient, if the location of the light(s) 108, 114, 116 as shown on the patient's skin begins to deviate from a generally vertical or straight pathway 120 when approximately 18 cm of the length L of the enteral tube 102 has been inserted into the patient, which is above the xiphoid process, the user of the system 100 (e.g., a health care provider) can conclude that the tube tip 106 is at or near the bifurcation zone 122. Further, the trachea T bifurcates into the left bronchi $B_L$ and the right bronchi $B_R$ past the bifurcation zone 122 and above the diaphragm D and xiphoid process. Therefore, referring to FIG. 6, if the light glowing through the patient's skin deviates from the generally vertical or straight pathway 120 past the bifurcation zone 122 but above the diaphragm D, e.g., into the patient's right bronchi $B_R$ as shown in FIG. 6, the user may determine that the tube tip 106 has entered the patient's airway and can correct the tube's position within the patient before continuing to insert the enteral tube 102. If, however, the user observes the light traveling along a generally vertical or straight path past the bifurcation zone 122 and near the diaphragm D, e.g., as illustrated in FIG. 7, the user may determine that the tube tip 106 is continuing on the correct pathway 120 (i.e., the tube 106 is within the esophagus rather than the trachea) to the patient's stomach S or bowel (not shown).

Additionally, the trachea T is anterior to the esophagus E. Thus, during placement of the enteral tube 102, if the tube 102 takes the path of the trachea T, there are fewer anatomical structures that the light from the light source(s) 108, 114, 116 must shine through to illuminate the patient's skin. Therefore, if the enteral tube 102 is in the trachea, the user of the system 100 would see a relatively bright light near the skin of the patient P, with little absorption from the patient's anatomy. Conversely, if the enteral tube 102 is placed into the intended pathway, the esophagus E, the light will need to transmit through much more anatomy than it would in the airway, i.e., the trachea T. As a result, when the tube 102 is properly placed in the esophagus E, the light would appear with a much lower intensity (compared to the intensity of the light when in the trachea T) or would not be visible at all, giving the user confidence that the enteral tube 102 is being placed in the correct location. Accordingly, the location and/or intensity of the one or more lights 108, 114, 116 as seen glowing on the surface of the patient's skin can indicate to the user of the system 100 whether the enteral tube 102 is being misplaced into the patient's airway, and if so, the user can correct the placement of the tube 102.

It will be appreciated that, whether the enteral tube 102 includes a single light source, such as the first light 108 embedded at or near the tube tip 106, or a plurality of light sources, such as first, second, and third lights 108, 114, 116 disposed at various positions along the tube 102, each light source should be capable of emitting light that can be transmitted through the patient's tissues and other anatomical structures. That is, each light source should have a lumen rating sufficient for the illuminated light source to be seen by the user on the patient's skin. As described above, the tube tip detection system 100 may be adapted for use in pediatric or adult patients, as well as non-human patients. Thus, in embodiments adapted for pediatric patients, the light source (s) embedded in the enteral tube 102 may have a different lumen rating (e.g., a lower lumen rating) than the light source(s) embedded in an enteral tube 102 for use in adult patients (which may have a higher lumen rating). Additionally or alternatively, more light sources may be used in a tube tip detection system 100 adapted for use in adult patients than a system 100 adapted for use in pediatric patients, e.g., to increase the likelihood that the light from the light sources will be able to pass through the adult patient's anatomical structures.

The present subject matter also provides methods for detecting a tube misplacement in a patient's airway. Referring now to FIG. 8, an exemplary method 200 is illustrated. As shown at 202 in FIG. 8, the method 200 comprises embedding a light source, such as first light 108, into an enteral tube 102. The enteral tube 102 is configured as described herein, having a proximal end 104 and a tip 106 separated by a length L of tubing. Moreover, the light source may be one or more LEDs or fiber optics as described above. As shown at 204 in FIG. 8, the method 200 also includes inserting the enteral tube 102 into the patient through the patient's nose or mouth. Thus, the enteral tube 102 may be a nasogastric or orogastric tube as described herein. Further, as shown at 206 and 208 in FIG. 8, the method 200 includes monitoring the location and/or intensity of the light source, e.g., first light 108, to determine if the enteral tube 102 is traveling into the patient's airway and, if so, then adjusting the location of the tube tip 106 such that it is no longer in the patient's airway.

It will be appreciated that, in other embodiments, the method 200 may accommodate other configurations of the tube tip detection system 100 as described in greater detail herein. For example, step 202 of the method 200 may comprise embedding a plurality of lights into the enteral tube 102, e.g., a first light 108 and a second light 114 as illustrated in FIG. 3 or a first, second, and third light 108, 114, 116 as illustrated in FIG. 4. Of course, the method 200 may vary to include other configurations of the apparatus and system described herein.

Accordingly, the present subject matter provides a system and apparatus for detecting the location of a tip of an enteral tube as it is inserted into a patient. In exemplary embodiments, the system uses one or more light sources on the tube that are illuminated as the tube is inserted into the patient such that a user of the system can monitor the location of the tube as it is inserted. By leaving or keeping the light source(s) illuminated during the entire placement, the user can continuously monitor the location of the enteral tube and, thereby, determine if the tube is inserted into the airway instead of traveling past the bifurcation of the patient's trachea from the patient's esophagus toward the gastrointestinal tract. The system may utilize a single light source, such as a single LED or end-emitting optical fibers, disposed on the tip of the tube to provide an indicator for determining the location of the tube tip within the patient. In other embodiments, the system utilizes a plurality of light sources disposed along the length of the tube to determine the location of the tube within the patient. The one or more light sources are illuminated as the enteral tube is inserted into the patient such that the light from the light source(s) is visible at the patient's skin, and a user of the system, e.g., a health care provider such as a physician, clinician, nurse, or other caregiver, can observe the light on the patient's skin to monitor the tube's location and thereby determine whether the tube tip is appropriately placed or is misplaced. Methods for detecting whether the tube tip is misplaced also are provided. Such methods, systems, and apparatus can help reduce the occurrence of misplaced enteral tubes, such as nasogastric or orogastric feeding tubes, thereby reducing complications from administering fluid to a patient through a misplaced tube. Further, the methods, systems, and apparatus described herein reduce such misplacements in a cost-efficient and time-efficient manner. More particularly, the light sources described herein are a relatively low-cost solution and are easily embedded in enteral tubes during the manufacture of the tubes. Moreover, the system described herein allows real-time, bedside verification of the tube placement, which can save time and money, e.g., compared to existing systems that require tube placement to be verified by x-ray or the like. Other benefits and advantages of the present subject matter also may be recognized by those of ordinary skill in the art.

It should also be appreciated that these procedures may involve treatment of humans by physicians, physician assistants, nurses, or other health care providers. In addition, these procedures may involve treatment of other mammals and animals by veterinarians, researchers, and others.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A tube tip detection system, comprising:
an enteral tube having a length, a tip, and a lumen defined through the enteral tube, the enteral tube defining a channel separate from the lumen, wherein the channel is defined on the exterior of the enteral tube;
a first light disposed at the tip, wherein the first light is disposed within the channel; and
a second light disposed along the length at a position within the channel and spaced apart from the tip, wherein a filler material is disposed within the channel around the first light and the second light such that the first and second lights are embedded within the channel, and
wherein the first and second lights are illuminated as the enteral tube is inserted into the patient to indicate to a user of the tube tip detection system whether the enteral tube is misplaced in the patient's airway, wherein the first and second lights comprise light emitting diodes.

2. The tube tip detection system of claim 1, further comprising:
a power source operatively connected to the first light for powering the first light.

3. The tube tip detection system of claim 1, wherein the first light comprises a plurality of optical fibers.

4. The tube tip detection system of claim 3, further comprising:
a light source operatively connected to the first light for transferring light along the plurality of optical fibers.

5. The tube tip detection system of claim 1, wherein the second light is disposed at a midpoint of the length.

6. The tube tip detection system of claim 1, wherein a third light is disposed along the length at a position spaced apart from the tip.

7. The tube tip detection system of claim 6, wherein the first light, the second light, and the third light are unequally spaced apart from one another.

8. The tube tip detection system of claim 6, wherein each of the first, second, and third lights comprise a light emitting diode.

9. The tube tip detection system of claim 6, wherein each of the first, second, and third lights comprise fiber optics.

10. The tube tip detection system of claim 1, further comprising:
a third light disposed within the channel.

11. The tube tip detection system of claim 1, wherein the enteral tube is a nasogastric tube.

12. An enteral tube, comprising:
a tip;
a length;
a lumen defined through the enteral tube;

a channel separate from the lumen, wherein the channel is defined on the exterior of the enteral tube; and a plurality of lights spaced apart from one another along the length within the channel, wherein a filler material is disposed within the channel along the plurality of lights such that the plurality of lights are embedded within the enteral tube.

wherein the plurality of lights comprises light emitting diodes, wherein each light of the plurality of lights is continuously illuminated as the enteral tube is inserted into the patient, and wherein a number of lights of the plurality of lights varies between pediatric patients and adult patients such that the number of lights is greater for adult patients than for pediatric patients.

13. The enteral tube of claim 12, wherein each light of the plurality of lights comprises a light emitting diode.

14. The enteral tube of claim 12, wherein each light of the plurality of lights comprises a plurality of optical fibers.

15. A method for detecting a tube misplacement in a patient's airway, comprising:

selecting a first light and a second light each having a lumen rating, wherein the first and second lights comprise light emitting diodes;

selecting an enteral tube having a lumen defined through the enteral tube;

forming a channel separate from the lumen on the exterior of the enteral tube;

disposing a filler material within the channel around the first and second lights such that the first and second lights are embedded in the channel of the enteral tube;

inserting the enteral tube into the patient through the patient's nose or mouth;

monitoring a location of the light as the enteral tube is inserted into the patient to determine if the enteral tube is traveling into the patient's airway, wherein the lumen rating varies between pediatric patients and adult patients such that the light has a lower lumen rating for pediatric patients than for adult patients.

\* \* \* \* \*